(12) United States Patent
Ogawa

(10) Patent No.: US 8,436,988 B2
(45) Date of Patent: May 7, 2013

(54) CLINICAL LABORATORY TEST APPARATUS

(75) Inventor: Yoshimasa Ogawa, Hyogo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 318 days.

(21) Appl. No.: 12/923,059

(22) Filed: Aug. 31, 2010

(65) Prior Publication Data
US 2011/0051133 A1    Mar. 3, 2011

(30) Foreign Application Priority Data
Sep. 1, 2009 (JP) .................. 2009-201274

(51) Int. Cl.
*G01N 1/10* (2006.01)

(52) U.S. Cl.
USPC .......................................... 356/246; 356/244

(58) Field of Classification Search ........... 356/244–246
See application file for complete search history.

(56) References Cited

U.S. PATENT DOCUMENTS
6,531,095 B2 * 3/2003 Hammer et al. ................. 422/64
8,004,670 B2 * 8/2011 Juhl .............................. 356/246

FOREIGN PATENT DOCUMENTS
JP        2007-322208 A    12/2007

* cited by examiner

*Primary Examiner* — Tara S Pajoohi Gomez
(74) *Attorney, Agent, or Firm* — Rader, Fishman & Grauer PLLC

(57) ABSTRACT

A clinical laboratory testing apparatus comprises a microchip for holding a sample liquid; a rotation body for rotating the microchip; a rotation drive mechanism; a lock mechanism for locking the microchip on the rotation body; a measurement room that holds the microchip and the rotation body; a protection cover; a light source that irradiates the measuring cell of the microchip; and a light receiving unit, wherein a centrifugal separation processing of a specimen in the sample liquid is performed in the microchip.

10 Claims, 12 Drawing Sheets

FIG. 1
FIG. 1A
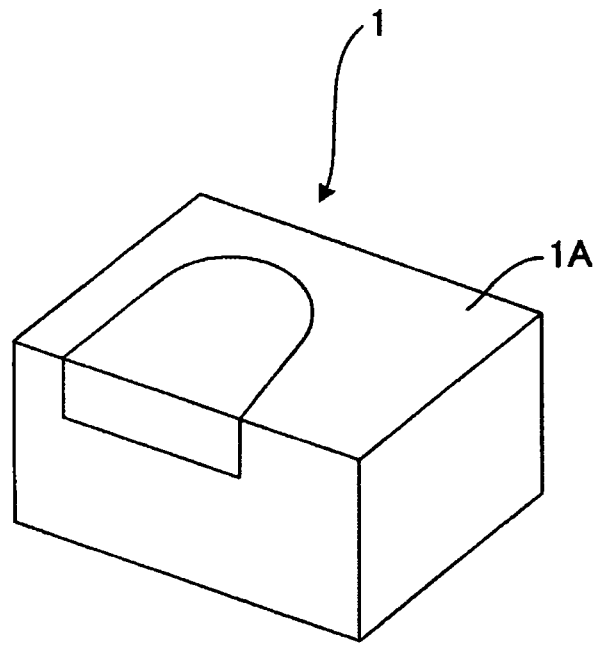
FIG. 1B
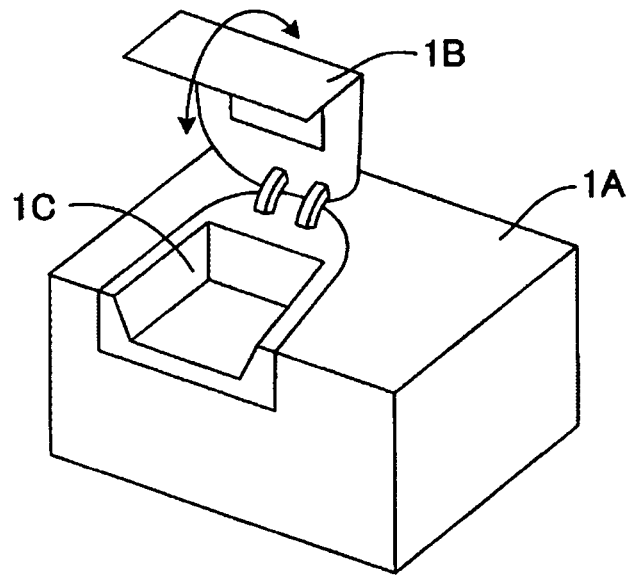

FIG. 7
FIG. 7A
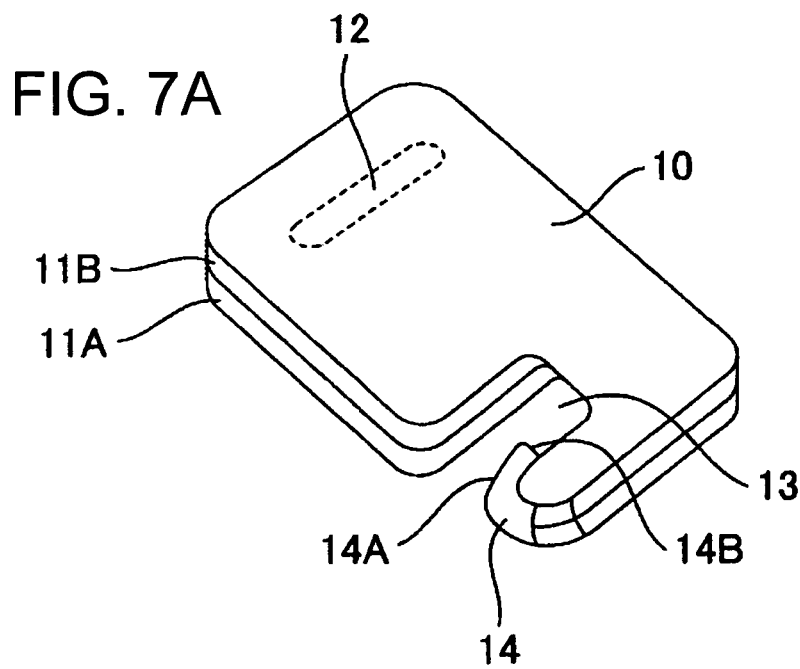
FIG. 7B
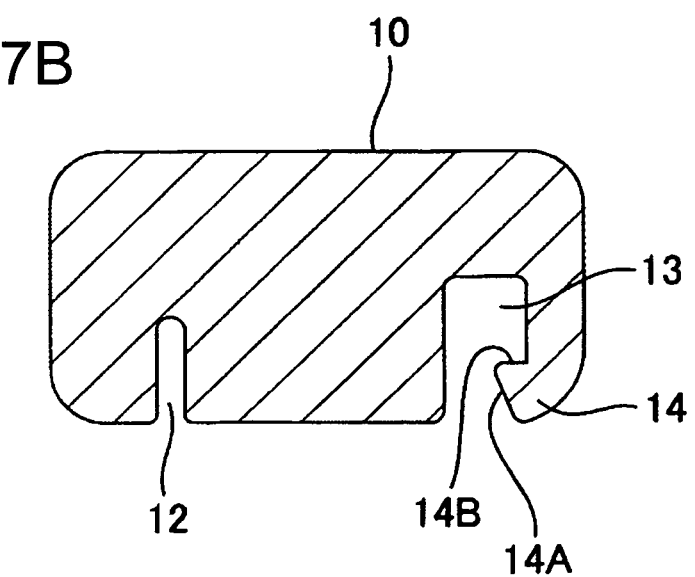

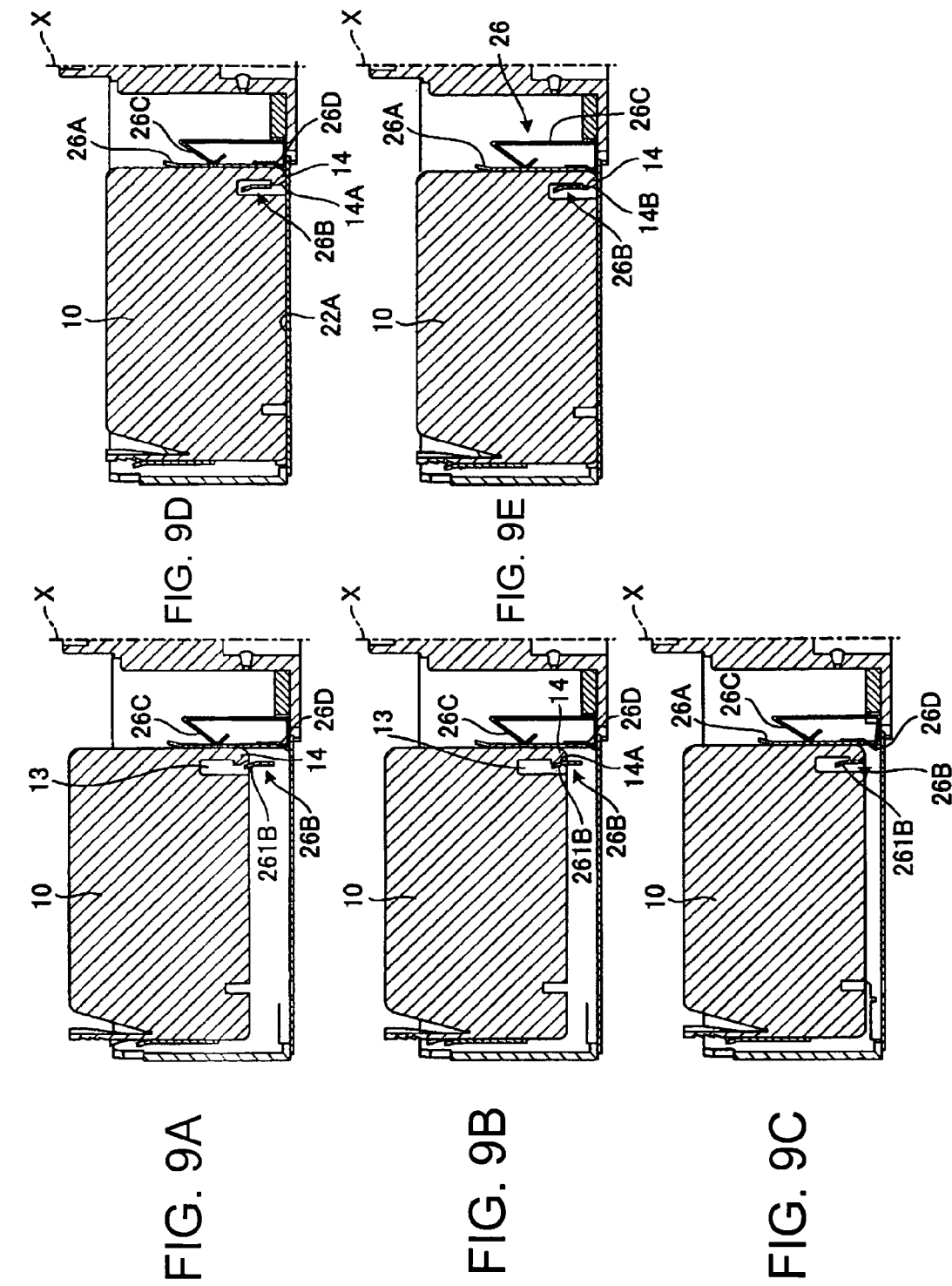

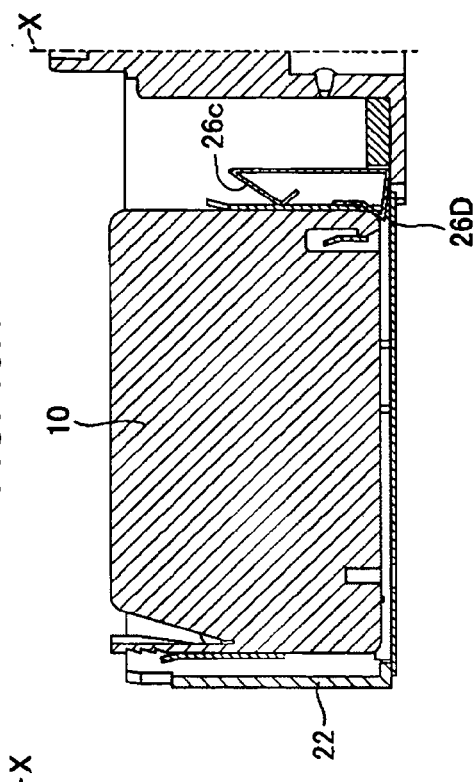
FIG. 10F
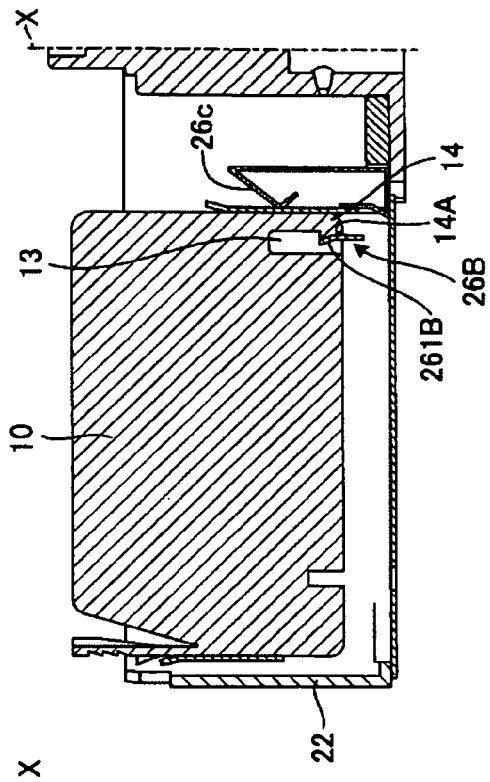
FIG. 10H
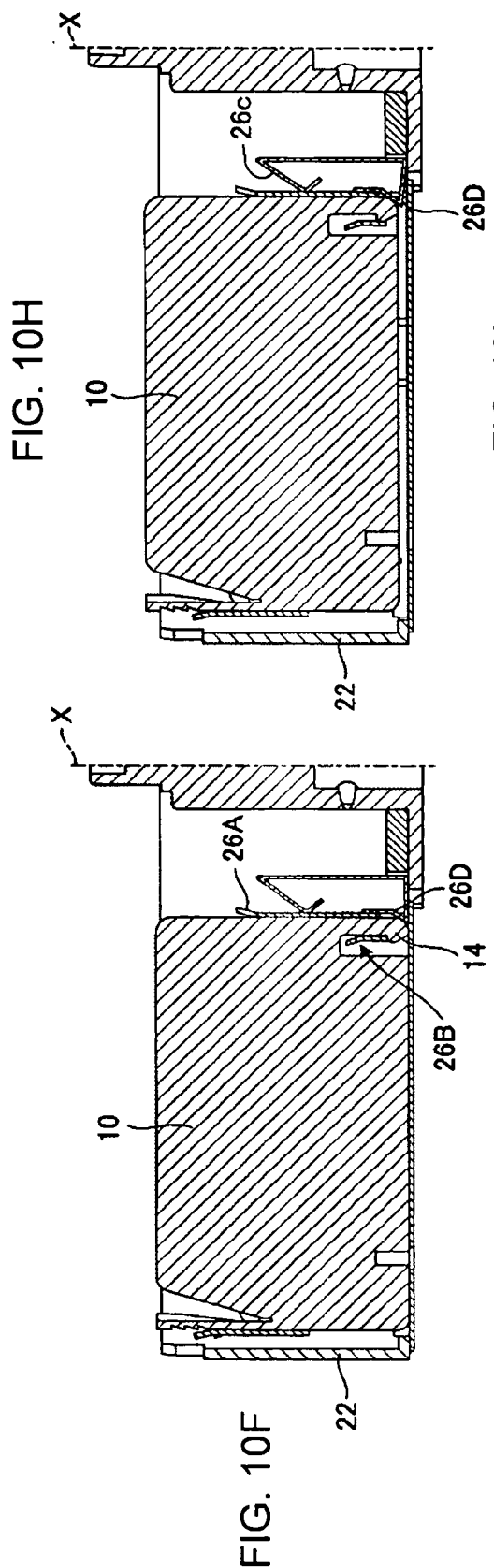
FIG. 10G
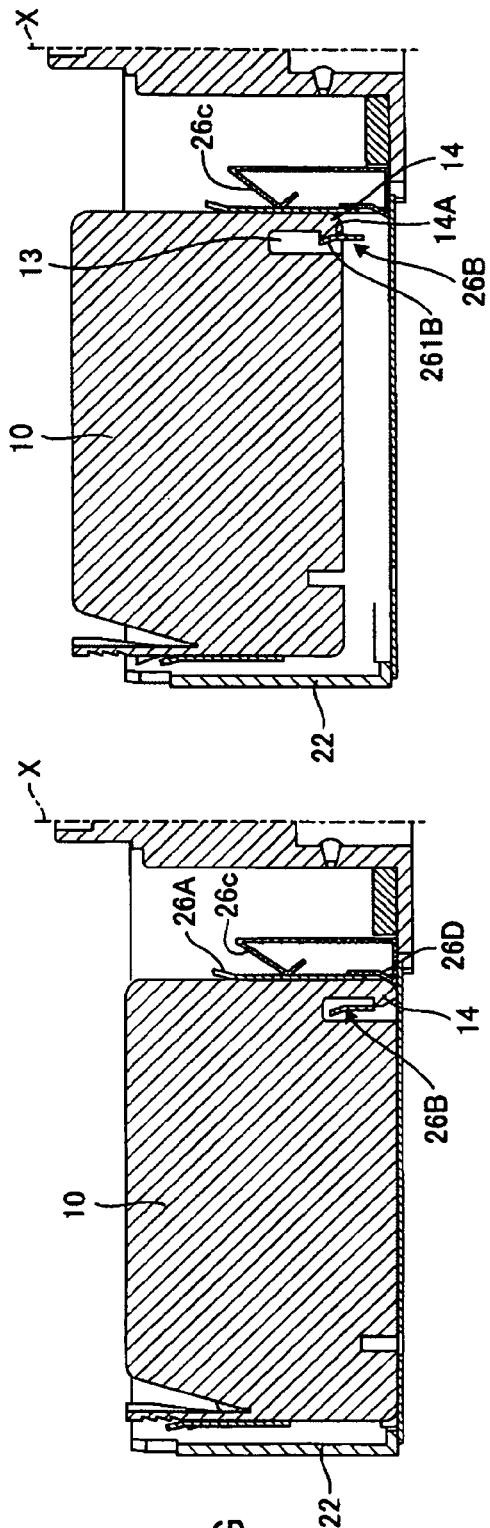
FIG. 10I
FIG. 10

Prior Art

CLINICAL LABORATORY TEST APPARATUS

CROSS-REFERENCES TO RELATED APPLICATION

This application claims priority from Japanese Patent Application Serial No. 2009-201274 filed Sep. 1, 2009, the contents of which are incorporated herein by reference in its entirety.

TECHNICAL FIELD

The present invention relates to a clinical laboratory test apparatus which performs centrifugal rotation of a microchip holding a sample such as blood, in order to measure the concentration of a component of an object to be detected, which is contained in the sample liquid held in the microchip.

BACKGROUND

In recent years, an analysis method using a microchip called "μ-TAS (μ-Total Analysis System)" or "Lab on a chip," which performs a chemical analysis, by applying the micromachine technology thereto, receives attention.

Such an analysis system, which uses such a microchip (hereinafter referred to as a microchip analysis system), aims at performing an entire process of an analysis including mixture, reaction, separation, extraction, and detection of a reagent in a fine flow path formed on a small substrate by the micromachine production technology. For example, in the medical field, such a system is used for an analysis of blood and an analysis of biomolecules, such as ultratrace protein and nucleic acid etc.

Especially, when human blood is analyzed, using the microchip analysis system, there are a variety of advantages, that is, (1) since the quantity of the blood (sample) needed for analysis and examination is small, a toll on its body can be reduced, (2) since the quantity of the reagent which is mixed with the blood and used therefor is small, analysis cost thereof can be reduced, (3) since the apparatus itself can be configured so as to be small, the analyze can be easily performed. Because of these advantages developments are increasing.

Generally, in such a microchip analysis system, for example, absorptiometry is a method used for measuring the concentration of a component of an object to be detected in the sample liquid. A clinical laboratory test apparatus using such absorptiometry, which is disclosed in Japanese Patent Application Publication No. 2007-No. 322208, is known.

FIG. 12 is a schematic cross-sectional view of an internal structure of a measurement unit of such a clinical examination analysis apparatus. The clinical laboratory test apparatus is equipped with a casing (not shown), wherein the measurement unit, a light source, and a light receiving unit are provided in the casing, as shown in FIG. 12. The measurement unit 100 has a measurement room 101, as shown in FIG. 12, and a rotation body 102, which is a cylinder with a bottom arranged in the measurement room 101. A driving shaft 103B arranged to penetrate the center of a lower face of the rotation body 102, extending in up and down directions and connected to a centrifugal motor 103A. The rotation body 102 is rotated by driving the centrifugal motor 103A. A rotation drive mechanism 103 is made up of the above-mentioned centrifugal motor 103A, the driving shaft 103B, and an encoder 103C, which is described below.

A gear 107 for a direction change, whose outer diameter is smaller than the radius of the rotation body 102, is provided in a bottom of the rotation body 102, wherein the gear 107 for a direction change is provided on the rotation body 102, and is rotatably supported by an axis thereof with respect to the axis parallel to the center of the rotational axis. A chip holding unit 106 for holding a microchip is provided on the gear 107 for a direction change. In addition, in FIG. 12, in order to maintain the rotation balance of the rotation body 102 in a proper state, another chip holding unit 106 that has the same structure as the above mentioned chip holding unit 106 is provided in the opposite side so that the rotational-axis center is located between these chip holding units 106.

An opening 101A for light guide and an aperture portion 102A, which guide light entering through a reflection mirror 132 from a light source 131 into a microchip measurement area (area where sample liquid is placed) in a state where the microchip is held by the chip holding unit 106 in a lower part of the measurement room 101, are formed in the rotation body 102 and the gear 107 for a direction change, to which the chip holding unit 106 are provided, respectively. A light receiving unit 133 receives light, which passes through the microchip measurement area. An optical fiber 134 guides the received light. An opening 101B for example is formed in an upper part of the measurement room 101 so as to place the light receiving unit 133 and the optical fiber 134.

It is necessary to perform an absorbance determination of a sample liquid in the microchip measurement area in a state where rotation of the rotation body 102 is stopped, and to guide the light from the above-mentioned light source 131 in the microchip measurement area. Therefore, it is necessary to precisely control the stop position of the rotation body 102. For this reason, the encoder 103C is connected to the centrifugal motor 103A, which rotates and drives the rotation body 102, and the stop position of the rotation body 102 is controlled based on a signal from the encoder 103C.

Moreover, a sheet heater 115 for keeping the temperature in a measurement room 101 constant (for example, 37 degrees Celsius) at the time of analysis and examination is formed in an area, which is part of an upper and lower faces of the measurement room 101. The heater 115 is controlled, based on the temperature detected by a temperature measuring unit 116 such as a thermistor, so that the temperature in the measurement room 101 becomes constant.

Moreover, in order to adjust the direction of the microchip held by the chip holding unit 106, the measurement unit 100 has a chip direction change mechanism 110, which has a drive mechanism separated from the rotation drive mechanism 103 for driving and rotating the rotation body. This chip direction change mechanism 110 comprises, for example, a driving side gear 113 that is provided rotatably with respect to the driving shaft 103B of the centrifugal motor 103A through a ball bearing 112 and that meshes with the gear 107 for a direction change, and a motor 111 for a chip direction change, which is a drive source for rotating and driving the driving side gear 113. The driving side gear 113 is rotated by driving the above-mentioned motor 111 for a chip direction change, so that the gear 107 for a direction change, and the chip holding unit 106 are rotated, whereby, the direction (direction with respect to the rotational-axis center of the rotation body 102) of the microchip can be changed.

For example, an analysis processing of the sample liquid is performed by the clinical laboratory test apparatus as set forth below. The rotation body 102, on which the microchip holding the sample (blood) is placed, is rotated, and a separation processing, which carries out centrifugal separation of the sample, is performed using a centrifugal force, and the sample liquid obtained by the separation processing is weighed. Further, a mixing and reaction treatment, which mixes and reacts the sample liquid to be measured and a reagent with each other, and a pretreatment operation including a processing for sending the liquid to be measured, which is obtained by the mixing and reaction treatment, to the measurement area, are performed.

Subsequently, the light receiving unit 133 receives light, which is guided from the light source 131 into the measurement area of the microchip, in a state where rotation of the rotation body 102 is stopped. Thereby, the amount of optical absorption is measured from the liquid to be measured, which is in the measurement area.

SUMMARY

The present invention relates to a clinical laboratory testing apparatus comprising a microchip having a measuring cell that holds a sample liquid; a rotation body; a rotation drive mechanism that rotates the rotation body; a lock mechanism that locks the microchip on the rotation body; a measurement room that holds the microchip and the rotation body and that has an attachment and detachment opening; a protection cover that closes the attachment and detachment opening; a light source that irradiates the measuring cell; and a light receiving unit that receives the light, wherein a centrifugal separation processing of a specimen in the sample liquid is performed in the microchip by the rotation drive mechanism rotating the rotation body, and wherein the protection cover has a pressing-down member that presses down a wall face of the microchip when the protection cover is closing the attachment and detachment opening.

BRIEF DESCRIPTION OF THE DRAWINGS

Other features and advantages of the present clinical laboratory test apparatus will be apparent from the ensuing description, taken in conjunction with the accompanying drawings, in which:

FIGS. 1A and 1B are appearance diagrams of a clinical laboratory testing apparatus according to the present invention;

FIG. 7A is a schematic perspective view of the structure of a microchip;

FIG. 7B is a cross sectional view of the structure of a microchip;

FIGS. 9A through 9E are partially enlarged cross sectional views for explaining an action of installing a microchip onto a lock mechanism;

FIGS. 10F through 10I are partially enlarged cross sectional views for explaining an action of removing a microchip from a lock mechanism;

DESCRIPTION

Figure 2:
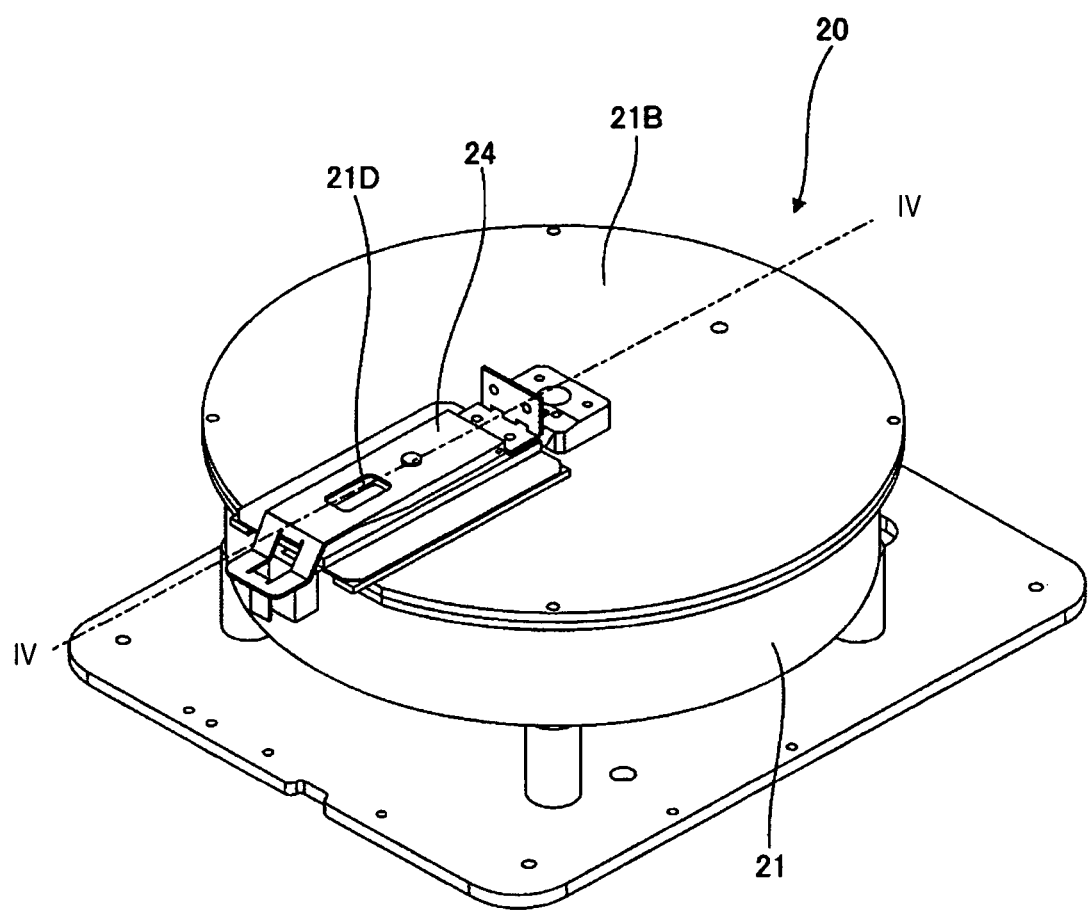
FIG. 2 is a perspective view of a test section of a clinical laboratory testing apparatus according to the present invention.

In recent years, the need for POCT (Point of care testing) are increasing. There are advantages to POCT, that is, an examination result can be obtained on that spot; a medical treatment and nursing can be performed based on the result on that examination date, and the patient can feel an examination close, so that it is possible to improve the medical care quality by the examination.

In order to use the above-mentioned clinical laboratory test apparatus for such a POCT examination, it is required to analyze a component of an object to be detected more quickly and more simply than the prior art. Especially, when components of a detected sample are analyzed with other examination items or when a single component of a detected sample for each of two or more persons is analyzed, a plurality of microchips is necessary.

When a living body sample, such as blood, which threatens infection, is analyzed, it is necessary to promptly discard the microchip after the analysis. Therefore, while the microchip is removed from the rotation body after every analysis, another microchip, which serves for the next analysis, is placed on the rotation body. When there are a large number of the microchips, which serve for analyses, operations for detaching each microchip from the rotation body and attaching it thereto are complicated.

Moreover, when a centrifugal separation processing of the microchip is performed, the microchip receives a great centrifugal force. When the center-of-gravity position of the microchip is located above in a vertical direction from the fulcrum point (fulcrum point in case of placement) of the microchip, a force, which tries to rise in an upper slanting direction with respect to the centrifugal direction of the microchip, is acted thereto. Therefore, in case where the centrifugal separation processing is performed, it is necessary to lock the microchip on the rotation body so that the microchip may not be separated from the rotation body. However, in the clinical laboratory test apparatus of the prior art, no consideration about how to simply and certainly attach a microchip to the rotation body is made.

It is an object of the present invention to offer a clinical laboratory test apparatus capable of simply and quickly attaching and detaching a microchip (s). According to the present invention, a clinical laboratory testing apparatus comprises a microchip having a measuring cell for holding a sample liquid to be examined; a rotation body on which the microchip is placed thereby rotating the microchip; a rotation drive mechanism, which rotates the rotation body, a lock mechanism, that locks the microchip on the rotation body; a measurement room in which the microchip and the rotation body are held and that has an attachment and detachment opening for detaching and attaching the microchip; a protection cover that closes up the attachment and detachment opening; a light source that irradiates the measuring cell of the microchip with light; and a light receiving unit that receives the light from the light source, wherein a centrifugal separation processing of a specimen in the sample liquid is performed in the microchip, by using a centrifugal force that acts when the rotation body is rotated by the rotation drive mechanism, and wherein the protection cover of the measurement room has a pressing-down member that presses down a wall face of the microchip, when the attachment and detachment opening of the measurement room is closed. In the clinical laboratory testing apparatus, the microchip has an opening extending perpendicularly to the rotation body, and a hook that is formed to project in a centrifugal direction of the rotation body in the wall face of the opening, in which the lock mechanism has an engaging portion for engaging with the hook, wherein when the microchip is pressed down by the pressing-down member, the engaging portion is inserted in the opening of the microchip whereby the engaging portion is engaged with the hook. In the clinical laboratory testing apparatus, the hook has a sliding surface that inclines, and the engaging portion has a sliding tip portion that slides on the sliding surface of the hook, wherein the lock mechanism comprises a first elastic portion that is pressed by the side face of the microchip when the engaging portion passes through the sliding face of the hook, and that biases the microchip in the centrifugal direction after the engaging portion passes through the hook and, a second elastic portion that is pressed by the bottom face of the microchip, and that biases the microchip in the centrifugal direction and in the upper side in the perpendicular direction after the engaging portion passes through the hook. In the clinical laboratory testing apparatus, the protection cover comprises two cover plates that are provided so as to be rotatable and independent of each other. A one cover plate is pivotally provided on the measurement room and has an opening through which the pressing-down member passes. An other cover plate is pivotally provided on the one cover plate, and has the pressing-down member. In the clinical laboratory testing apparatus, the other cover plate has a contact portion, which is in contact with the one cover plate. In the clinical laboratory testing apparatus, the one cover plate is depressed by the contact portion provided on the other cover plate, so as to close up the attachment and detachment opening of the measurement room. In the clinical laboratory testing apparatus, the measurement room has a cover lock mechanism that locks the one cover plate. In the clinical laboratory testing apparatus, only the one cover plate is locked by the cover lock mechanism. In the clinical laboratory testing apparatus, the pressing-down member, which is provided on the other cover plate, has a pressing-down pin that is in contact with a upper wall face of the microchip, and an elastic member, which is connected to the pressing-down pin and which is held between the one cover plate and the other cover plate. In the clinical laboratory testing apparatus, the pressing-down pin provided on the other cover plate receives a repulsive force generated when the elastic member is pressed down to be biased towards an upper side in a vertical direction. In the clinical laboratory testing apparatus, the pressing-down pin has a full length so as to be in contact with the upper wall face of the microchip when the one cover plate is locked on the cover lock mechanism of the measurement room. In the clinical laboratory testing apparatus, the microchip is arranged in an orientation in which a side face area of the microchip becomes larger than a base area thereof. In the clinical laboratory testing apparatus, two or more of the microchips are placed on the rotation body.

According to the clinical laboratory test apparatus of the present invention, only by performing a very easy operation of closing the attachment and detachment opening by the protection cover provided in the measurement room, the microchip is pressed down by the pressing-down member, so that the microchip can be attached to the lock mechanism on the rotation body. Therefore, it is possible to simply and certainly attach the microchip thereto.

FIGS. 1-4 are diagrams showing the configuration structure of a clinical laboratory testing apparatus of the present invention. FIGS. 1A and 1B are appearance diagrams of a clinical laboratory testing apparatus. Specifically, FIG. 1A shows a closed state, and FIG. 1B shows an open state for inserting a microchip of the clinical laboratory testing apparatus is seen. As shown in FIG. 1A, the clinical laboratory testing apparatus 1 has a casing 1A. When a microchip is inserted into the clinical laboratory testing apparatus, as shown in FIG. 1B, the lid 1B of the casing 1A is opened, and the microchip is put in a measurement room (refer to FIG. 2) from the opening 1C, which is formed in the casing 1A.

Figure 3:
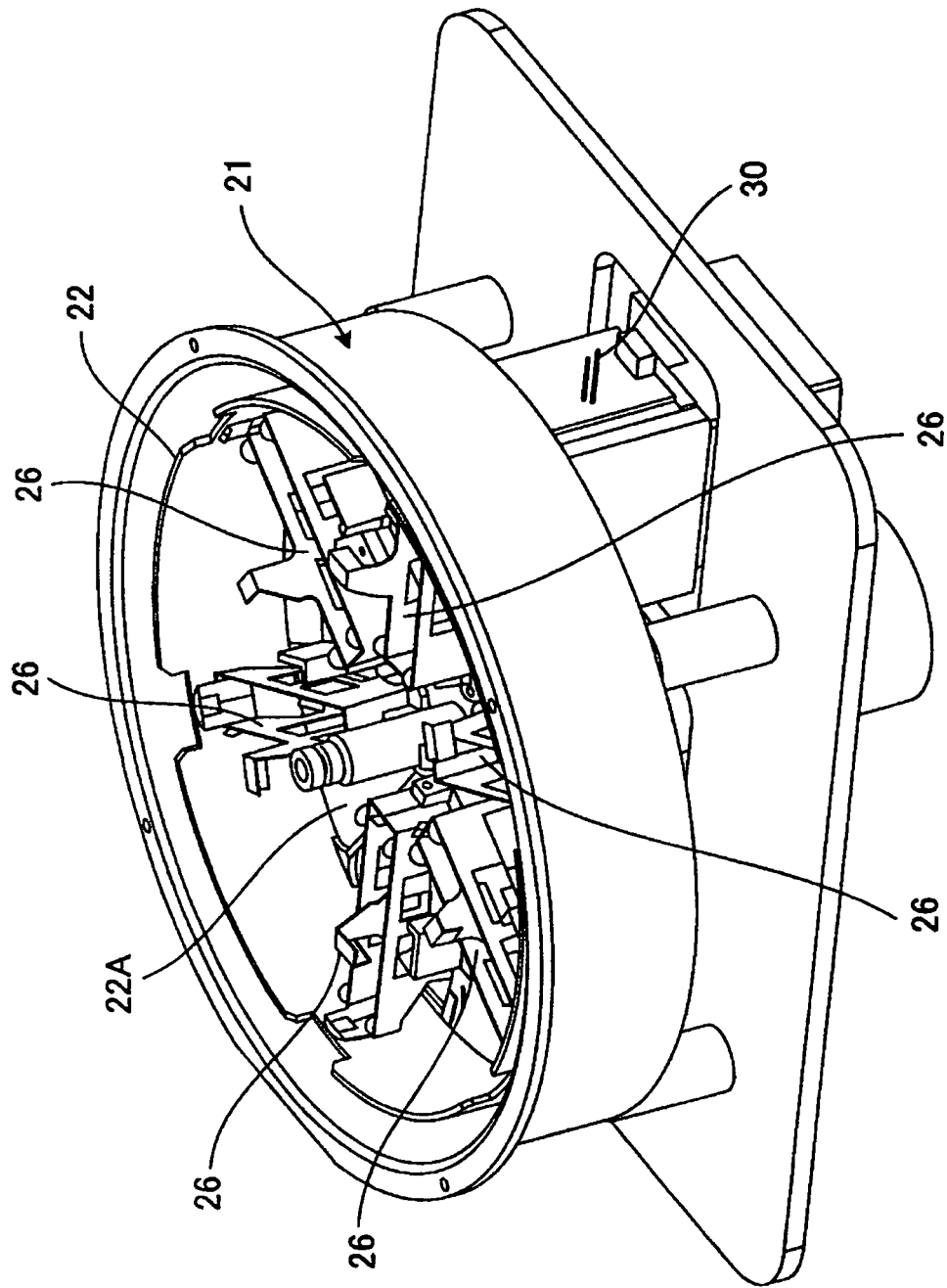
FIG. 3 is a perspective view of an internal structure of a test section of a clinical laboratory testing apparatus according to the present invention.
Figure 4:
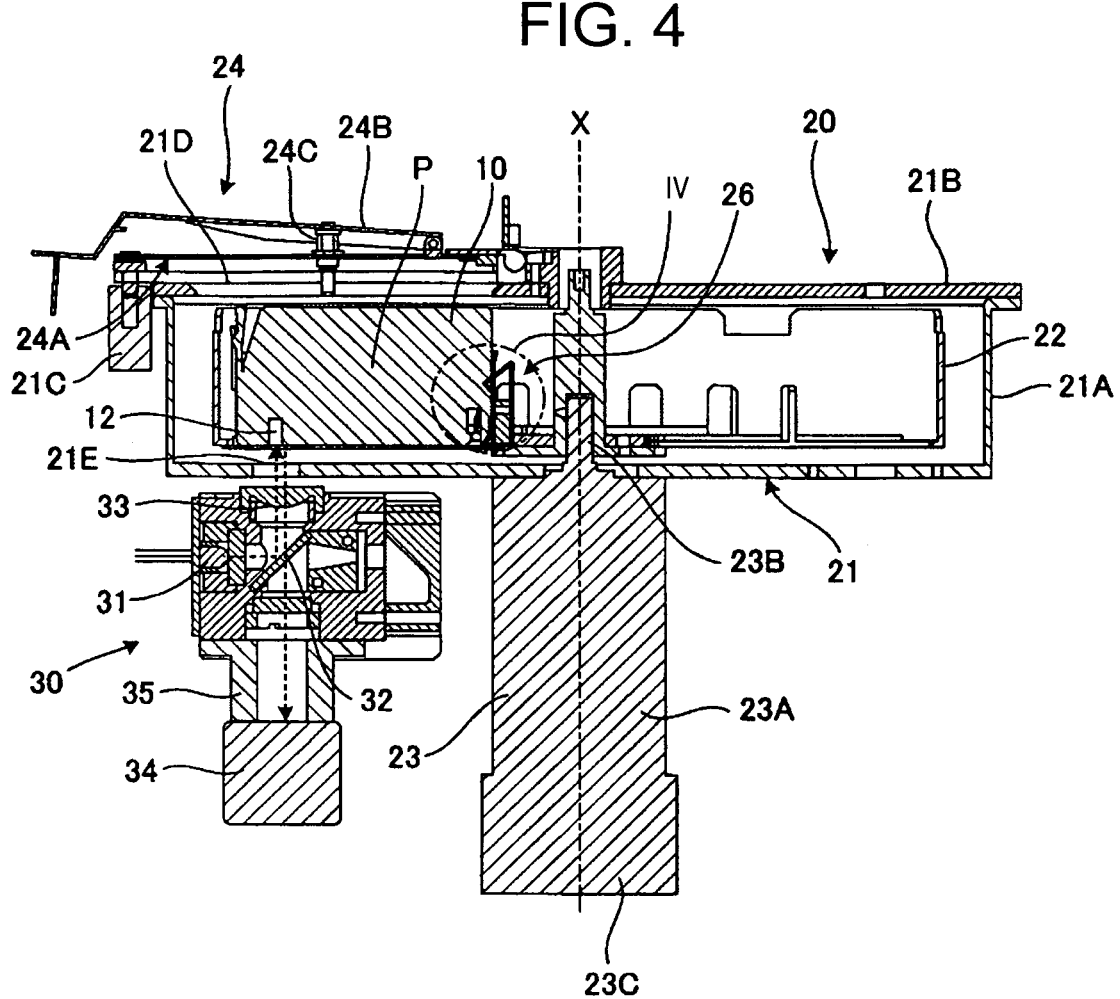
FIG. 4 is a cross sectional view thereof taken along a line IV-IV of FIG. 2.

FIGS. 2-4 are drawings showing the structure of a test section 20 arranged in the inside of the casing 1A shown in FIGS. 1A and 1B. Specifically, FIG. 2 is a perspective view showing the test section 20, FIG. 3 is a perspective view showing the internal structure of the test section 20, and FIG. 4 is a cross sectional view thereof, taken along a line IV-IV of FIG. 2. In addition, in FIG. 3, a top board portion of the test section 20 is removed.

The test section 20 of the clinical laboratory testing apparatus comprises the measurement room 21 that has a hollow cylinder shape, a rotation body 22 arranged inside the measurement room 21, a rotation drive mechanism 23 that rotates and drives the rotation body 22, and a protection cover 24 that closes an attachment and detachment opening 21D of the measurement room 21. As shown in FIG. 4, a centrifugal motor 23A of the rotation drive mechanism 23 is connected through a driving shaft 23B with the rotation body 22, so that the rotation body 22 is rotated and driven by the centrifugal motor 23A. In the centrifugal motor 23A, an encoder 23C for detecting the rotational position thereof is provided.

As shown in FIG. 3, the rotation body 22 placed in the measurement room 21 has a cylinder shape with a bottom, and an outer diameter thereof, slightly smaller than that of the measurement room 21. Lock mechanisms 26 whose number is the same as that of microchips (6 (six) in FIG. 3,) are provided on a bottom face 22A of the rotation body 22. The lock mechanisms 26 prevent the microchips from coming off from the rotation body 22 at time of a centrifugation separation processing by locking the microchips on the rotation body 22.

As shown in FIG. 4, the measurement room 21 has a cylindrical portion 21A having a bottom, the top board portion 21B that closes an opening of the cylindrical portion 21A having a bottom, and a holding portion 21C that is a cover lock mechanism for locking the protection cover 24. The single attachment and detachment opening 21D for detaching and attaching the microchip(s) is formed in the top board portion 21B.

The number of the microchips to be placed on the rotation body 22 is set up suitably if needed. By using a number of microchips, it is possible to efficiently measure a number of object components to be detected or a single detection object component for each of two or more persons. When placing two or more microchips on the rotation body 22, every time every microchip is fixed to the lock mechanism 26 (shown in FIG. 3), the rotation body 22 is rotated and driven in a state that the protection covering 24 is closed so that the attachment and detachment opening 21D (shown in FIG. 2) is closed, and a next lock mechanism 26 is moved to right under the attachment and detachment opening 21D.

As shown in FIG. 4, a light guide opening 21E and an aperture (not shown), which transmit light entering through a reflection mirror 32 from a light source 31, are respectively formed in a lower part of the measurement room 21 and the rotation body 22. As shown in FIG. 4, a box shape light source unit 30, which emits light towards the measuring cell of the microchip 10 and which measures fluorescence emitted from a sample liquid held in the microchip 10, is provided in the lower part of the measurement room 21. As shown in FIG. 4, the light source unit 30 comprises a light source 31; a half mirror 32 that is arranged to incline with respect to an optical axis on an optical path of the light emitted from the light source 31; a lens 33, which is on the optical path of the light reflected by the half mirror 32 and which is arranged near the light guide opening 21E; a light receiving unit 34 which detects the light emitted from the sample liquid held in the measurement cell 12 of the microchip 10; and a casing 35 that holds the light source 31, the half mirror 32, the lens 33, and the light receiving unit 34. In addition, although it is described below that the light source unit 30 analyzes the fluorescence emitted from the sample liquid held in the microchip 10, it may analyze absorption of light instead of analysis of fluorescence.

The light source 31 is a green light emitting diode, which emits green light with a wave length of 525 nm. The half mirror 32 reflects the green light emitted from the diode 31 in a direction of the lens 33, and transmits the fluorescence (yellowish green light) emitted from the sample liquid held in the measurement cell 12 of the microchip 10. The lens 33, whose convex face faces the half mirror 32, is a plano-convex lens. The light receiving unit 34 detects the intensity of the fluorescence (yellowish green light) emitted from the sample liquid held in the measurement cell 12 of the microchip 10. The light receiving unit 34 sends out a signal as to the intensity of the fluorescence emitted from the sample liquid to a control unit (not shown). Based on the signal, the control unit (not shown) calculates the concentration of the object component to be detected in sample liquid.

For example, an analysis processing of the sample liquid by the clinical laboratory testing apparatus of the present invention is performed as described bellow. As shown in FIG. 4, the rotation body 22, on which the microchip 10 holding the sample liquid (blood) is placed, is rotated, and a separating process, in which centrifugal separation of the sample liquid is carried out using a centrifugal force, is performed, whereby liquid to be measured, which is obtained by the separating process, is weighed. A mixing and reaction treatment in which the liquid to be measured and a reagent are mixed with each other for reaction, is performed, and then a pretreatment operation including the processing for sending the liquid to be measured, which is obtained in the mixing and reaction treatment, into the measurement cell 12, is performed. Subsequently, the light from the light source 31 is guided into the measurement cell 12 of the microchip 10. The light source 31 irradiates, with green light, the liquid to be measured, with which the measurement cell 12 is filled up, so that yellow-green fluorescence is emitted therefrom. The light receiving unit 34 detects the intensity of the yellow-green fluorescence. The concentration of a component of an object to be detected, which is contained in the liquid to be measured (with which the measurement cell 12 is filled up), is obtained based on the intensity of the fluorescence.

Figure 5:
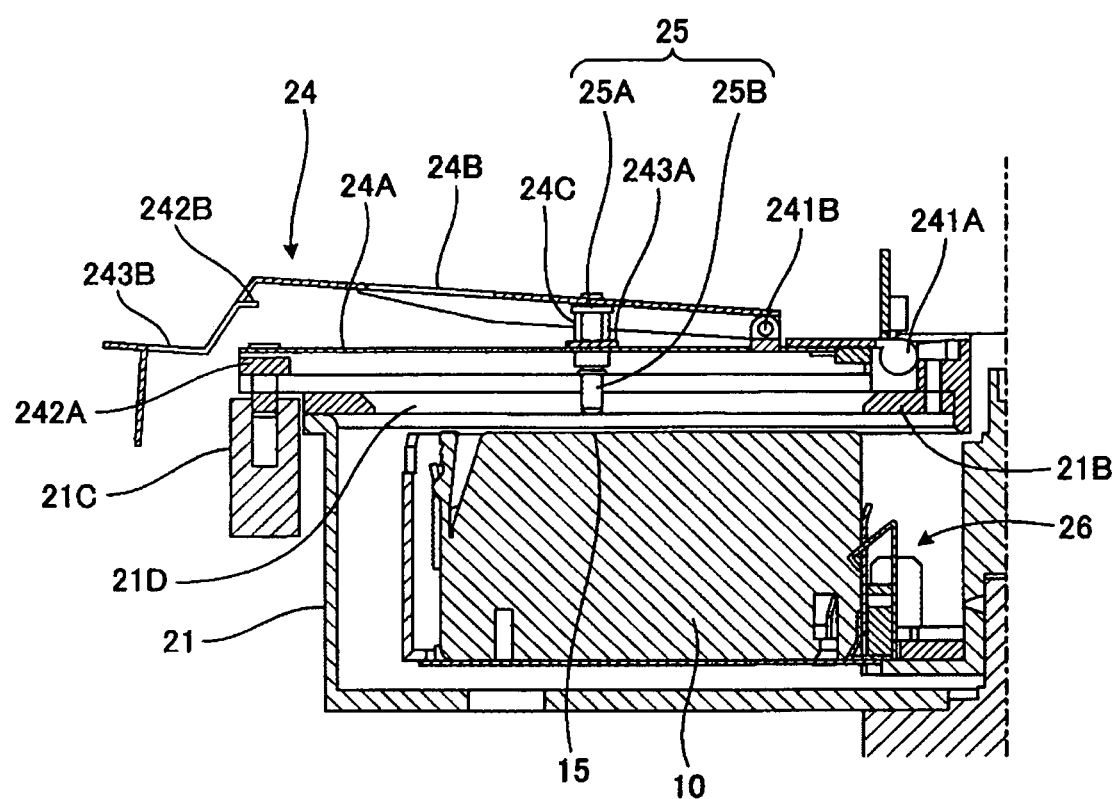
FIG. 5 is a partially enlarged cross sectional view of the structure of a protection cover.

Next, a description of the protection cover 24 will be given below. FIG. 5 is a partially enlarged cross sectional view of the structure of the protection cover 24 shown in FIG. 4. As shown in FIG. 5, the protection cover 24 for closing the attachment and detachment opening 21D is provided on the top board portion 21B of the measurement room 21. The protection cover 24 presses down the microchip 10 through a pressing-down member 25 so as to attach the microchip to the lock mechanism 26. As shown in FIG. 5, the protection cover 24 has an one cover plate 24A, which is rotatable by 90 degrees in a circumferential direction (hereinafter referred to as a cover plate 24A), and an other cover plate 24B (hereinafter referred to as a cover plate 24B), wherein the cover plates 24A and 24B are rotatable independently of each other.

A hinge 241A is provided in an end portion in a longitudinal direction of the cover plate 24A and is pivotally held by (with respect to) the top board portion 21B of the measurement room 21. A projection portion 242A for locking the cover plate 24A to the measurement room 21 is provided in the other end portion in the longitudinal direction of the cover plate 24A. Furthermore, a through-hole, in which a sleeve 243A having a shape of a cylinder is inserted, is formed approximately in the center of the cover plate 24A in the longitudinal direction, so that the pressing-down pin 25B penetrates there through.

A hinge 241B is provided at one end of the cover plate 24B in a longitudinal direction, and the cover plate 24B is pivotally held by the cover plate 24A. The pressing-down member 25, which extends perpendicularly with respect to the cover plate 24B, is provided in a portion that is close to the hinge 241B in the longitudinal direction of the cover plate 24B. A contact portion 242B, which is pressed against the other end portion of the cover plate 24A when the cover plate 24B is depressed, is provided on the cover plate 24B. The contact portion 242B is provided in a portion where the cover plate 24B is certainly brought in contact with the cover plate 24A when the cover plate 24B is depressed. Since the contact portion 242B is provided to certainly lock it in the holding portion 21C of the measurement room 21 when the cover plate 24A is depressed. In order to easily perform opening and closing operations of the cover plate, an operating portion 243B is provided at the other end of the cover plate 24B in the longitudinal direction.

Figure 8:
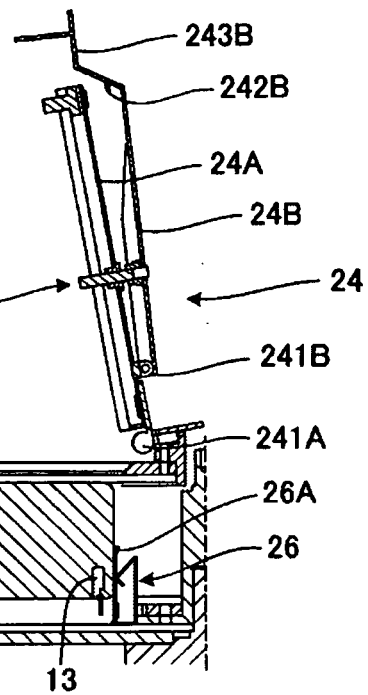
FIGS. 8A, 8B, and 8C are cross sectional views thereof for explaining an action of a protection cover.
Figure 8A:
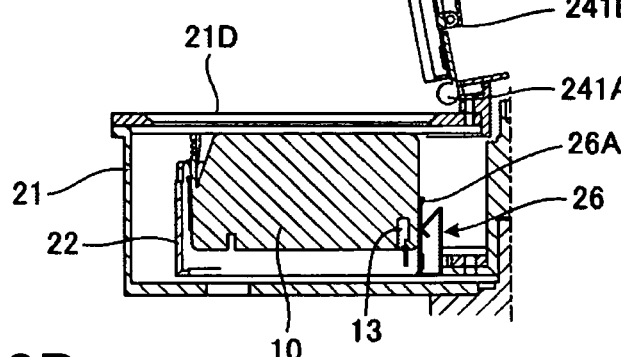
Figure 8B:
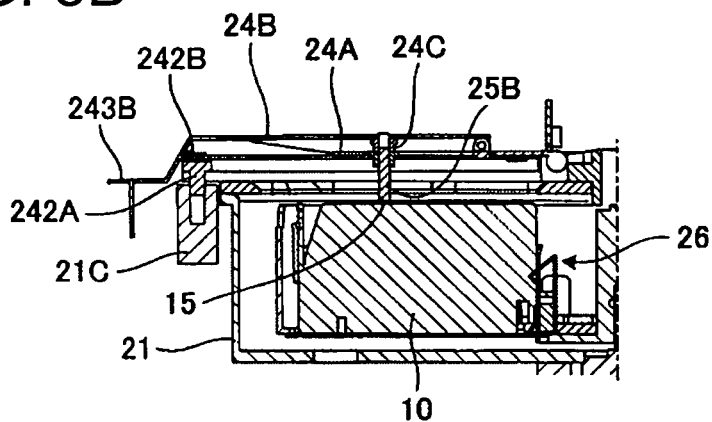

When the protection cover 24 is closed, the operating portion 243B of the other cover plate 24B is held and the cover plate 24B is pressed down in a vertical direction, so that the contact portion 242B is pressed against the other end portion of the cover plate 24A (refer to FIG. 8B). In this way, the projection portion 242A having a shape of T character, which is provided in the one cover plate 24A, is depressed by the contact portion 242B of the other cover plate 24B, the projection portion 242A is inserted in the holding portion 21C, so that only the one cover plate 24A is locked by the holding portion 21C (refer to FIG. 8B). Thus, when a centrifugal separation processing of the sample liquid held in the microchip 10 is performed, the protection cover 24 may not be opened since the cover plate 24A is locked in the holding portion 21C.

As shown in FIG. 5, an elastic member 24C is provided between the cover plate 24A and the cover plate 24B, which form the protection cover 24, and, thus, held by the cover plate 24A and the cover plate 24B. The pressing-down pin 25B is inserted with a gap inside the elastic member 24C. The elastic member 24C is formed by, for example, a spring.

As shown in FIG. 5, the pressing-down member 25 comprises a holding member 25A, which has a shape of cylinder having a bottom and fixes it to the cover plate 24B, and the cylindrical pressing-down pin 25B, which is inserted in the holding member 25A. While the pressing-down pin 25B is inserted with a gap inside the elastic member 24C so as to penetrate through the elastic member 24C, wherein one end of the pressing-down pin 25B is inserted in the holding member 25A, and the other end passes through the sleeve 243A provided in the one cover plate 24A so as to project under the one cover plate 24A. The pressing-down pin 25B has the overall length in contact with a wall face of the microchip 10 when the one cover plate 24A is locked to the measurement room 21 (refer to FIG. 8B).

When the cover plate 24A of the protection cover 24 is locked on the measurement room 21, the elastic member 24C is pressed up and down by the cover plate 24A and the cover plate 24B, thereby producing repulsive force. Since the cover plate 24B is not locked by the measurement room 21 when the cover plate 24A is locked on the measurement room 21, it is biased upward in a vertical direction by the repulsive force of the elastic member 24C. With this operation, the pressing-down pin 25B provided on the cover plate 24B is biased upward in the vertical direction simultaneously with the cover plate 24B, so that the pressing-down pin 25B goes into a state where the pin 25B is separated from an upper wall face 15 of the microchip 10 (refer to FIG. 8C).

That is, although the pressing-down pin 25B presses down the microchip 10 when the microchip 10 is locked in the lock mechanism 26, after the lock of the microchip 10 is completed, the pressing-down pin 25B moves back from the upper wall face 15 of the microchip 10 by the repulsion force of the elastic member 24C. That is, the pressing-down pin 25B can move in the up-and-down direction. Therefore, when the pressing-down pin 25B performs a centrifugal separation processing of the sample liquid held in the microchip 10, the pressing-down pin 25B does not interferes with the processing.

As shown in FIG. 4, the pressing-down pin 25B is arranged so that the pressing-down pin 25B presses down the upper wall face 15 of the microchip 10 in a vertical direction near the center-of-gravity P of the microchip 10. Since the microchip 10 can be attached to the lock mechanism 26 without applying excessive pressure, if the pressing-down pin 25B is arranged in this way, a load added to the rotation body 22 can be suppressed.

Figure 6:
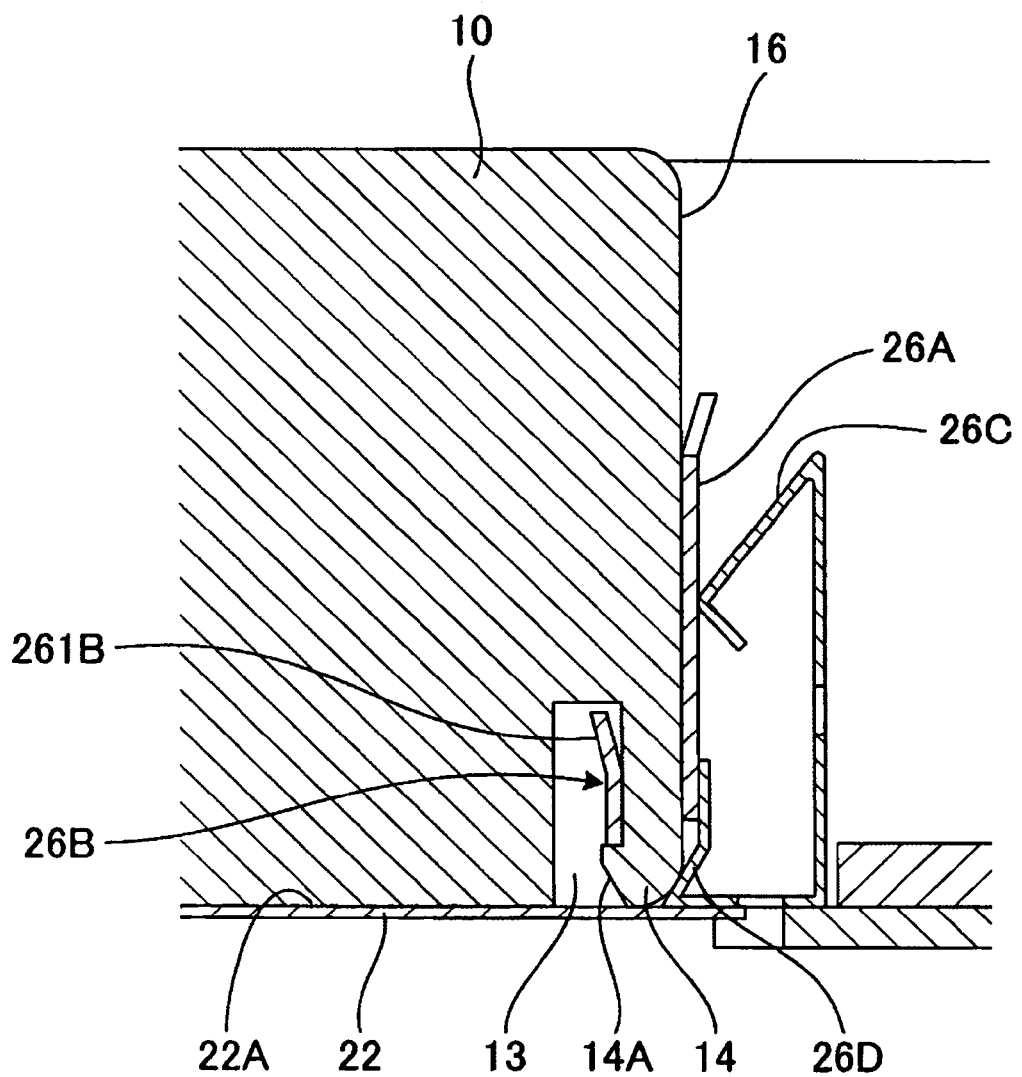
FIG. 6 is an enlarged view of a portion VI of FIG. 4.

Next, description of the lock mechanism 26, which locks the microchip 10, will be given below. FIG. 6 is a partially enlarged view of a portion VI shown in FIG. 4. As shown in FIG. 6, the lock mechanism 26 comprises a cylindrical frame body 26A having a rectangular cylinder shape, which contains the microchip 10 therein, an engaging portion 26B that is engaged with the hook (shown in FIG. 7) formed in the microchip 10, a first elastic portion 26C that presses a frame body 26A in a centrifugal direction (a left side direction of FIG. 6), and a second elastic portion 26D that biases the microchip 10 in the centrifugal direction and upward in the vertical direction.

The frame body 26A can be moved while holding the microchip 10, that is, the frame body 26A can be moved in a diameter direction of the rotation body 22, when the microchip 10 is detached or attached. The engaging portion 26 has a sliding tip portion 261B, which inclines in a centrifugal direction. As shown in FIG. 6, the first elastic portion 26C is arranged in contact with a side face of the frame body 26A. As described below, when the microchip 10 is detached or attached, the side face 16 of the microchip 10 presses the first elastic portion 26C through the frame body 26A, thereby biasing the microchip 10 in the direction of centrifugality. The second elastic portion 26D inclines by 45 degrees towards the rotational axis from a bottom face 22A. As described above, the second elastic portion 26D is provides so that the microchip is biased in the direction of centrifugality and in an upward direction in the vertical direction when the hook 14 (shown in FIG. 7) of the microchip 10 presses through the second elastic portion 26D in case where the microchip is detached or attached.

These first elastic portion 26C and the second elastic portion 26D are preferably formed of a blade spring. When blade springs which are excellent in a repulsion force, are used as the first elastic portion 26C and the second elastic portion 26D, since the microchip 10 can more certainly be locked in the rotation body 22, it is possible to prevent the microchip 10 from coming off from the rotation body 22, while performing a centrifugal separation processing of a component of an object to be detected in the sample liquid. In addition, although the first elastic portion 26C and the second elastic portion 26D are integrally formed with each other in the embodiment shown in FIG. 6, they may be formed by components which are separated from each other.

As shown in FIG. 4, the engaging portion 26B, the first elastic portion 26C, and the second elastic portion 26D, are provided closer to the rotational-axis X than the center-of-gravity position P of the microchip. Therefore, in such a case, it is possible to certainly prevent the microchip from coming off when performing the centrifugal separation processing of the component of the object to be detected in the sample liquid of the microchip 10, compared with the case where they are provided so as to be closer than the center-of-gravity position P of the microchip in the centrifugal direction.

Next, description of the microchip used in the clinical laboratory test apparatus according to the present invention will be given below. FIGS. 7A and 7B are schematic views of the structure of the microchip. Specifically, FIG. 7A is a perspective view of the external appearance of the microchip, and FIG. 7B is a cross sectional view of the microchip, taken along in the longitudinal direction thereof. As shown in FIG. 7A, the microchip 10 is formed by putting a substrate 11B in which no flow path is formed, over one substrate 11A in which a flow path including a measurement cell 12, a separation cell (not shown), and a mixing cell (not shown) are formed, and bonding the one substrate 11A and the other substrate 11B with each other.

Furthermore, as shown in FIG. 7B, an opening 13 and the hook 14 are formed in order to lock the microchip 10 in the above-mentioned lock mechanism 26. As shown in FIG. 6, the opening 13 is formed so as to extend in a direction perpendicular to the rotation body 22, and the hook 14 is formed so as to project in a centrifugal direction in an inner wall of the opening 13. The hook 14 has a sliding face 14A that inclines in the centrifugal direction from an opening end of the opening 13 towards an inside of the opening, and a flat portion 14B that is continuously formed from the sliding face 14A and which extends in parallel with a bottom face 22A of the rotation body 22. The sliding face 14A is formed approximately in parallel with the sliding tip portion 261B of the engaging portion 26B (as shown in FIG. 6). The first elastic portion 26C shown in FIG. 6 is pressed, when the sliding tip portion 261B slides on the sliding face 14A.

Figure 8C:
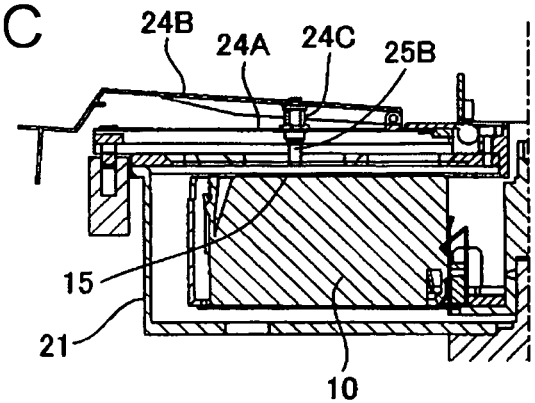

Next, description of an attachment and detachment method of the microchip 10 in the clinical laboratory test apparatus according to the present invention will be given below, referring to FIGS. 8A-8C, 9A-9E, 10F-10I, and FIG. 11. FIGS. 8A, 8B and 8C are cross sectional views for explaining an action of a protection cover. Specifically, FIG. 8A shows a state where the protection cover 24 is in an open state, FIG. 8B shows a state where the wall face of the microchip 10 is pressed down by the pressing-down member 25, and FIG. 8C shows a state where the pressing-down member 25 is retracted from the wall face of the microchip 10. FIGS. 9A-9E are partially enlarged cross sectional views for explaining an action of installing the microchip 10 on the lock mechanism 26. FIGS. 10E-10I are partially enlarged cross sectional views for explaining an action of removing the microchip 11 from the lock mechanism 26.

Description of an operation for installing the microchip 10 on the lock mechanism 26. As shown in FIG. 8A, an operator installing the microchip 10 opens the protection cover 24 and inserts the microchip 10 of the measurement room from the attachment and detachment opening 21D. The microchip 10 is placed inside the frame body 26A so that the opening 13 is located in a downside in a vertical direction.

Next, as shown in FIG. 8B, an operator holds the operating portion 243B of the cover plate 24B, rotates the cover plate 24B counterclockwise by 90 degrees with respect to hinge 241A, and brings this contact portion 242B of the cover plate 24B in contact with the other end portion of the cover plate 24A. Thereby, as shown in FIG. 8B, the projection portion 242A having a shape of T character, which is provided on the cover plate 24A, is inserted in the holding portion 21C of the measurement room 21, and the cover plate 24A is locked by the measurement room 21. As described above, the tip portion of the pressing-down pin 25B provided on the cover plate 24B is brought in contact with the upper wall face 15 of the microchip 10, and presses down the microchip 10, by locking the cover plate 24A on the measurement room 21. As described above, when the microchip 10 is pressed down by the pressing-down pin 25B, the microchip 10 is attached to the lock mechanism 26, as set forth below.

As shown in FIG. 9A through 9C, the frame body 26A, which contains the microchip 10, moves in the rotational-axis X direction when the sliding tip portion 261B of the engaging portion 26B moves towards the inside of the opening 13 while sliding on the sliding face 14A of the hook 14. When the microchip 10 moves to the position shown in FIG. 9C, the frame body 26A presses the first elastic portion 26C. As shown in FIG. 9D, when the entire engaging portion 26B slips through the sliding face 14A, the hook 14 presses the second elastic portion 26D. Since the second elastic portion 26D has the shape such that it inclines by 45 degrees with respect to the bottom face 22 of the rotation body 22 (refer to FIG. 6), when the hook 14 presses the second elastic portion 26D, a repulsion force, which biases the microchip 10 in the centrifugal direction and in an upward direction in the vertical direction, is generated. Finally, as shown in FIG. 9E, a base end portion of the engaging portion 26B is engaged with the flat portion 14B of the hook 14, so that the microchip 10 is locked by the lock mechanism 26, whereby the attachment of the microchip 10 is completed. Thus, in the clinical laboratory test apparatus according to the present invention, the pressing-down pin 25B presses down the upper wall face 15 of the microchip 10 by merely depressing the cover plate 24B and locking the cover plate 24A on the measurement room 21, whereby attachment of the microchip 10 to the lock mechanism 26 is completed.

Figure 11:
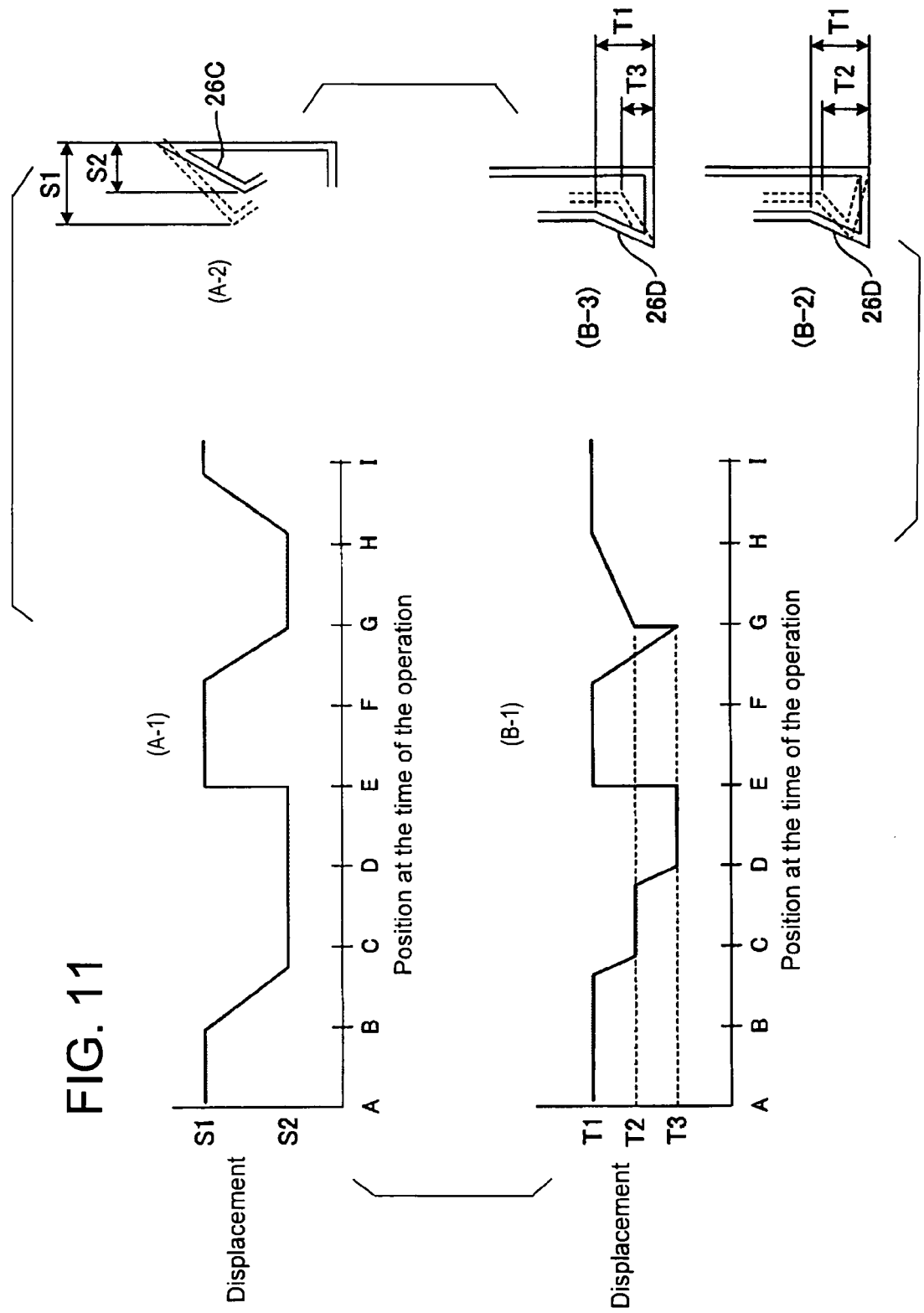
FIG. 11 is a diagram for explaining a deformation of a first elastic portion and a second elastic portion due to attachment and detachment actions of a microchip.
Figure 12:
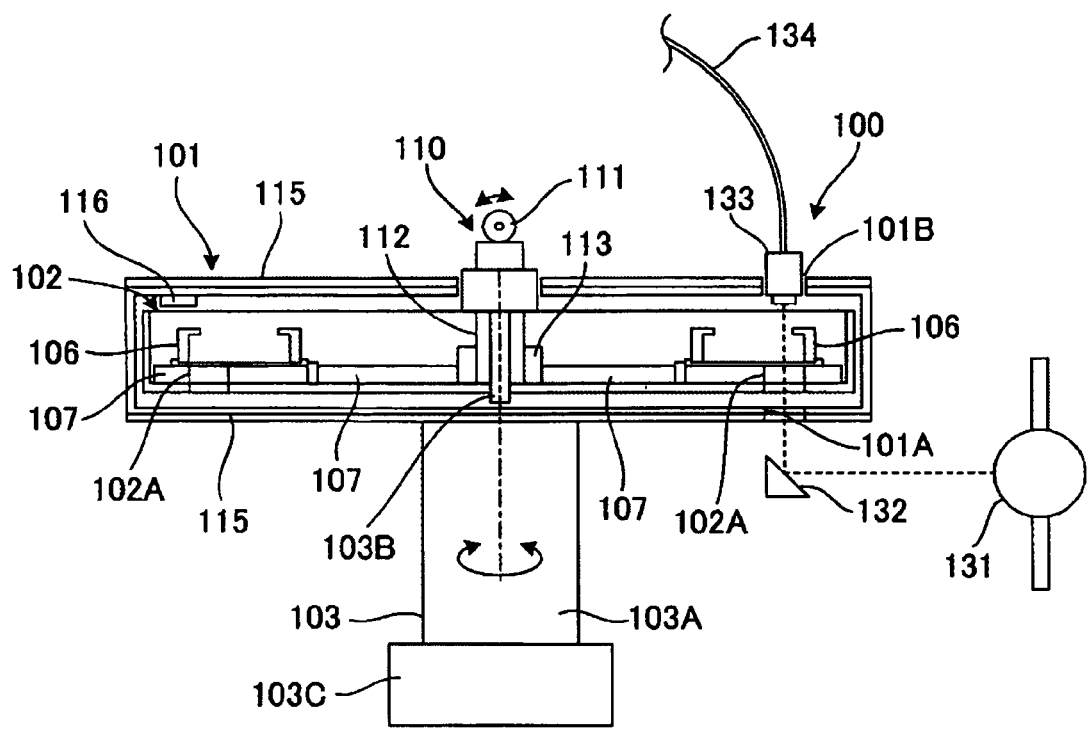
FIG. 12 is a diagram showing a cross sectional view of the structure of a test section of a conventional clinical laboratory testing apparatus.

FIG. 11 is a diagram for schematically explaining a deformation of the first elastic portion 26C and the second elastic portion 26D. In FIG. 11 (A-1), a vertical axis shows displacement of the first elastic portion 26C, and a horizontal axis shows the position of the microchip 10. In FIG. 11 (B-1), a vertical axis shows displacement of the second elastic portion 26D and a horizontal axis shows the position of the microchip 10. FIG. 11 (A-2) shows a state where the first elastic portion 26C is displaced, and FIG. 11 (B-2) shows a state where the second elastic portion 26D is displaced. Referring to FIG. 11, an operation of the first and second elastic portions at time of attachment of the microchip 10 is described below.

When the microchip 10 is in the position shown in FIGS. 9A and 9B, the first elastic portion 26C has not been displaced, as shown as a position A-B of FIG. 11 (A-1). When the microchip 10 moves to the position shown in FIG. 9C, the above-mentioned frame body 26A presses the first elastic portion 26C. At this time, as shown as a position B-C of FIG. 11 (A-1) and FIG. 11 (A-2), while the first elastic portion 26C is displaced from S1 to S2, as shown as a position B-C of FIG. 11 (B-1) and FIG. 11 (B-2), the second elastic portion 26D is displaced from T1 to T2. When the microchip 10 moves to the position shown in FIG. 9D, the first elastic portion 26C is pressed by the frame body 26A, and the second elastic portion 26D is pressed by the hook 14 of the microchip 10. The first elastic portion 260 is in the state of S2, as shown as a position D of FIG. 11 (A-1). As shown as the position D of FIG. 11 (B-1) and FIG. 11 (B-3), the second elastic portion 26D is displaced to T3. The first elastic portion 26C, which is pressed by the frame body 26A, biases the frame body 26A in the centrifugal direction, and as shown as a position E of FIG. 11 (A-1) and FIG. 11 (A-2), the first elastic portion 26C is displaced from S2 to S1. At the same time, the second elastic portion 26D biases the frame body 26A in the centrifugal direction, and as shown as a position E of FIG. 11 (B-1) and FIG. 11 (B-3), the second elastic portion 26D is displaced from T3 to T1.

When performing the centrifugal separation processing of a component of an object to be detected in the sample liquid held in the microchip 10 after the microchip 10 is attached to the lock mechanism 26, in order that the pressing-down pin 25B does not interfere, it is necessary to move the pressing-down pin 25B away from the upper wall face 15 of the microchip 10. As shown FIG. 8B, in a state where the pressing-down pin 25B is in contact with the upper wall face 15 of the microchip 10, the elastic member 24C is sandwiched and pressed by both of the cover plate 24A and the cover plate 24B from an upside and a downside. Therefore, after the microchip 10 is attached to the lock mechanism 26 of the microchip 10, if the operator releases his or her hand from the cover plate 24B, as shown in FIG. 8C, the cover plate 24B receives a repulsion force by the elastic member 24C, so as to be biased upward in the vertical direction, so that the pressing-down pin 25B fixed to the cover plate 24B is biased simultaneously with the cover plate 24B toward an upper side thereof in the vertical direction, whereby as shown in FIG. 8C, the pressing-down pin 25B is moved away from the upper wall face 15 of the microchip 10.

Then, description of an operation for removing the microchip 10 from the lock mechanism 26 will be given below. The operator unlocks the cover plate 24A that is locked by the measurement room 21 (FIG. 8C), and rotates the cover plate 24A and the cover plate 24B clockwise by 90 degrees, so that the protection cover 24 is arranged in the position shown in FIG. 8A, and the attachment and detachment opening 21D of the measurement room 21 is opened. The operator moves the microchip 10 from a state shown in FIG. 10F to a state shown in FIG. 10F, and presses the frame body 26A, which contains the microchip 10, in the rotational-axis X direction of the rotation body 22. When the microchip 10 is moved to the position of FIG. 10G, while the engagement state between the engaging portion 26B and the hook 14 is canceled so that the first elastic portion 26C is pressed through the frame body 26A, the hook 14 of the microchip 10 presses the second elastic portion 26D. As shown in FIG. 10H, the microchip 10 receives a repulsion force by the second elastic portion 26D so as to be biased upward in the vertical direction, and the microchip 10 moves along with the frame body 26A upward in the vertical direction, while resisting the elastic power of the first elastic portion 26C. As shown in FIG. 10I, the sliding face 14A of the hook 14 slides on the sliding tip portion 261B of the engaging portion 26B in the centrifugal direction, whereby the microchip 10 receives a repulsion force from the first elastic portion 26C, so as to be biased in the centrifugal direction. Finally, the engaging portion 26 is pulled out from the opening 13 of the microchip 10, and the operator can hold the microchip 10 by hand and take out from the attachment and detachment opening 21D (refer to FIG. 2) of the measurement room 21.

Referring to FIG. 11, description of an operation of the first and second elastic portions when the microchip 10 is removed will be given below. When the microchip 10 moves to the position of FIG. 10G, the frame body 26A presses the first elastic portion 26C. At this time, as shown as a position F-G of FIG. 11 (A-1) and FIG. 11 (A-2), while the first elastic portion 26C is displaced from S1 to S2, as shown as a position F-G of FIG. 11 (B-1) and FIG. 11 (B-3), the second elastic portion 26D is displaced from T1 to T2. When the microchip 10 moves to the position shown in FIG. 10H, as shown as a position G-H of FIG. 11 (A-1), while the first elastic portion 26C is in a state of S2, the second elastic portion 26D biases the microchip 10 upward in the vertical direction. At this time, as shown as a position G-H of FIG. 11 (B-1), and FIG. 11 (B-2) and FIG. 11 (B-3), the second elastic portion 26D is displaced from T3 to T2 and then T2 to T1 in that order. When the microchip 10 moves to the position shown in FIG. 10I, the first elastic portion 26C biases the microchip 10 in the direction of centrifugality. At this time, as shown as a position I of FIG. 11 (A-1), and FIG. 11 (A-2), the first elastic portion 26C is displaced from S2 to S1.

In the clinical laboratory test apparatus according to the present invention, effects set forth below can be expected.

(1) The microchip 10 can certainly be locked on the rotation body 22 by performing a very simple operation. That is, merely by performing a very simple operation of closing the attachment and detachment opening 21D for the microchip by the protection cover 24 (the one cover plate 24A), the microchip 10 is pressed down by the pressing-down member 25, so that the microchip 10 can be certainly attached on the lock mechanism 26.

(2) The microchip 10 is certainly locked, so that in case of a centrifugal separation processing of a sample liquid, there is no possibility that the microchip comes off from the rotation body 22. That is, when the microchip 10 is pressed down by the pressing-down member 25, the hook 14 provided on the microchip 10 engages with the engaging portion 26B provided on the lock mechanism 26. Since the hook 14 engages with the engaging portion 26B when performing a centrifugal separation processing of the sample liquid held by the microchip 10, it is possible to prevent the microchip 10 from rising due to the centrifugal force, so that there is no possibility that the microchip 10 may come off from the rotation body 22.

(3) When performing a centrifugal separation processing of the sample liquid, the pressing-down member 25, which presses down the microchip 10, does not interfere with the centrifugal separation processing. That is, the pressing-down member 25 comprises the elastic member 24C, which is held between the one cover plate 24A and the other cover plate 24B, and the pressing-down pin 25B, which is connected therewith. After the microchip 10 is attached to the lock mechanism 26, by using a repulsion force produced when the one cover plate 24A and the other cover plate 24B press the elastic member 24C, the pressing-down pin 25B is biased upward in the vertical direction, it is possible to certainly prevent the pressing-down pin 25B from interfering with the centrifugal separation processing.

The preceding description has been presented only to illustrate and describe exemplary embodiments of the present clinical laboratory test apparatus. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A clinical laboratory testing apparatus, comprising:
   a microchip having a measuring cell that holds a sample liquid;
   a rotation body;
   a rotation drive mechanism that rotates the rotation body;
   a lock mechanism that locks the microchip on the rotation body;
   a measurement room that holds the microchip and the rotation body and that has an attachment and detachment opening;
   a protection cover that closes the attachment and detachment opening;
   a light source that irradiates the measuring cell;
   a light receiving unit that receives the light; and
   a hook that is formed to project in a centrifugal direction of the rotation body in the wall face of the opening,
   wherein a centrifugal separation processing of a specimen in the sample liquid is performed in the microchip by the rotation drive mechanism rotating the rotation body,
   wherein the protection cover has a pressing-down member that presses down a wall face of the microchip when the protection cover is closing the attachment and detachment opening,
   wherein the microchip has an opening extending perpendicularly to the rotation body,
   wherein the lock mechanism has an engaging portion that engages with the hook, and
   wherein the engaging portion is inserted in the opening of the microchip so that the engaging portion is engaged with the hook when the microchip is pressed down by the pressing-down member.

2. The clinical laboratory testing apparatus according to claim 1, wherein the hook has a sliding surface that inclines,
   wherein the engaging portion has a sliding tip portion that slides on the sliding surface of the hook, and
   wherein the lock mechanism comprises:
      a first elastic portion that is pressed by the side face of the microchip when the engaging portion passes through the sliding face of the hook and that biases the microchip in the centrifugal direction after the engaging portion passes through the hook; and
      a second elastic portion that is pressed by the bottom face of the microchip and that biases the microchip in the centrifugal direction and in the upper side in the perpendicular direction after the engaging portion passes through the hook.

3. A clinical laboratory testing apparatus comprising:
   a microchip having a measuring cell that holds a sample liquid;
   a rotation body;
   a rotation drive mechanism that rotates the rotation body;
   a lock mechanism that locks the microchip on the rotation body;
   a measurement room that holds the microchip and the rotation body and that has an attachment and detachment opening;
   a protection cover that closes the attachment and detachment opening;
   a light source that irradiates the measuring cell; and a light receiving unit that receives the light, wherein a centrifugal separation processing of a specimen in the sample liquid is performed in the microchip by the rotation drive mechanism rotating the rotation body, wherein the protection cover has a pressing-down member that presses down a wall face of the microchip when the protection cover is closing the attachment and detachment opening, wherein the protection cover comprises:
 a one cover plate; and
 an other cover plate, wherein the one cover plate and the other cover plate are rotatable and independent of each other, wherein the one cover plate is pivotally provided on the measurement room and has an opening through which the pressing-down member passes, and wherein the other cover plate is pivotally provided on the one cover plate and has the pressing-down member.

4. The clinical laboratory testing apparatus according to claim 3, wherein the other cover plate has a contact portion that is in contact with the one cover plate.

5. The clinical laboratory testing apparatus according to claim 4, wherein the one cover plate is pressed by the contact portion provided on the other cover plate, to close up the attachment and detachment opening.

6. The clinical laboratory testing apparatus according to claim 5, wherein the measurement room has a cover lock mechanism that locks the one cover plate.

7. The clinical laboratory testing apparatus according to claim 6, wherein only the one cover plate is locked on the cover lock mechanism.

8. The clinical laboratory testing apparatus according to claim 3, wherein the pressing-down member that is provided in the other cover plate has a pressing-down pin that is in contact with the upper wall face of the microchip and an elastic member that is connected to the pressing-down pin and that is held between the one cover plate and the other cover plate.

9. The clinical laboratory testing apparatus according to claim 8, wherein the pressing-down pin provided on the other cover plate receives a repulsive force generated when the elastic member is pressed down, so as to be biased in an upper side in a vertical direction.

10. The clinical laboratory testing apparatus according to claim 8, wherein the pressing-down pin has a full length in contact with the upper wall face of the microchip when the one cover plate is locked on the cover lock mechanism.

\* \* \* \* \*